United States Patent [19]

Jones

[11] 3,972,884
[45] Aug. 3, 1976

[54] D-HOMO-AZA-STEROIDS
[75] Inventor: Charles D. Jones, Indianapolis, Ind.
[73] Assignee: Eli Lilly and Company, Indianapolis, Ind.
[22] Filed: Sept. 6, 1974
[21] Appl. No.: 503,564

[52] U.S. Cl. .................... 260/287 AZ; 260/286 R; 260/289 AZ; 424/258
[51] Int. Cl.² .................................. C07D 215/12
[58] Field of Search .................. 260/289 AZ, 287 R

[56] References Cited
UNITED STATES PATENTS
3,845,203   10/1974   Williams et al. .................... 424/122

OTHER PUBLICATIONS
Tsuda et al., "Jacs," 1956, pp. 4107-4111.
Morrison et al., "Organic Chemistry," 1966, pp. 581-582.
March et al., "Advanced Organic Chemistry," 1968, pp. 890-892.

Primary Examiner—Nicholas S. Rizzo
Assistant Examiner—David E. Wheeler
Attorney, Agent, or Firm—Charles W. Ashbrook; Everet F. Smith

[57] ABSTRACT

New 14a-aza-D-homo-cholestane derivatives are useful as antifungal agents.

17 Claims, No Drawings

D-HOMO-AZA-STEROIDS

BACKGROUND OF THE INVENTION

An extensive amount of research has been devoted to the isolation and preparation of agents useful in treating infectious diseases in both man and animal. Although there are many diseases that are now controllable with agents such as the penicillin or cephalosporin antibiotics, there are still an alarming number of infectious diseases which plague mankind. For example, several infections caused by the pathogenic fungi, especially those infections caused by the various species of *Candida*, including *C. tropicalis* and *C. albicans*, are not easily controlled.

A new group of antibiotics which are particularly active against pathogenic fungi has recently been discovered and is the subject of co-pending U.S. patent application Ser. No. 327,171, filed Feb. 2, 1973, entitled ANTIBIOTIC A-25822 AND PROCESS FOR PRODUCTION THEREOF. The new antibiotics are nitrogen-containing steroid-like compounds.

It is an object of this invention to provide novel compounds which are derivatives of the above-mentioned antibiotics and which compounds are useful as antifungal agents.

SUMMARY OF THE INVENTION

The present invention relates to new nitrogen-containing compounds which are structurally related to cholestane. More particularly, the invention provides compounds having the formula

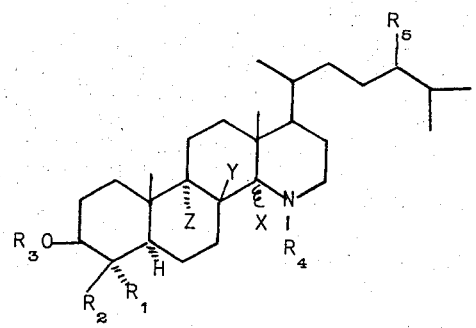

I in which $R_1$ and $R_2$ are both hydrogen or both methyl; $R_3$ and $R_4$ independently are hydrogen, $C_1$–$C_4$ alkanoyl, $C_1$–$C_4$ alkoxycarbonyl, or halo $C_1$–$C_4$ alkoxycarbonyl; $R_4$ is additionally $C_1$–$C_4$ alkyl, and X is hydrogen, or when taken together, $R_4$ and X form a double bond; and Y and Z are both hydrogen or taken together form a double bond. Either X or both Y and Z must be hydrogen. $R_5$ is methyl or methylene, but is methyl only when X, Y and Z are all hydrogen. Also included within the scope of this invention are the non-toxic pharmaceutically acceptable acid addition salts of the basic compounds of the invention. In addition, the quaternary salts, obtained by treating the amines or imines with a lower alkyl alkylating agent, are included herein.

The compounds of this invention are prepared by selectively reducing the centers of unsaturation of a naturally occurring 24-methylene-D-homo-aza-steroid diene. The compounds provided by this invention are useful in combating diseases of fungal origin.

DETAILED DESCRIPTION OF THE INVENTION

The compounds provided by this invention are nitrogen-containing steroid-like compounds having the above formula.

In the present specification and claims, the term "$C_1$–$C_4$ alkanoyl" refers to groups such as formyl, acetyl, propionyl, butyryl and isobutyryl. Examples of $C_1$–$C_4$ alkoxycarbonyl include methoxycarbonyl, ethoxycarbonyl, isopropoxycarbonyl, tert.-butoxycarbonyl, and the like. "Halo" refers herein to fluoro, chloro, bromo, and iodo, and typical halo $C_1$–$C_4$ alkoxycarbonyl groups include fluoromethoxycarbonyl, 2-bromoethoxycarbonyl, 2,2,2-trichloroethoxycarbonyl, 2-bromoisobutoxycarbonyl, and related groups.

$R_4$ of the above formula can be a $C_1$–$C_4$ alkyl group such as methyl, ethyl, propyl, butyl, isobutyl, or the like.

The organic bases of this invention generally form pharmaceutically acceptable salts with a variety of inorganic and organic acids. The particular acid used in salt formation is not critical; however, the salt that is formed should be substantially non-toxic to animal organisms. Typical examples of acids which are routinely used in salt formation include mineral acids such as hydrochloric, hydrobromic, hydroiodic, sulfuric, phosphoric, and like acids. Examples of organic acids often used include formic, acetic, citric, succinic, benzoic, maleic, and related acids. Additionally, certain organic bases provided herein form quaternary ammonium salts or quaternary immonium salts with a variety of alkylating agents such as methyl iodide, ethyl chloride, allyl bromide, methyl sulfate, propyl toluenesulfonate, and the like. It should be understood that salt formation occurs only when the nitrogen atom is of a sufficiently basic nature to react with a suitable salt forming reagent. When $R_4$ of the above formula is alkanoyl, alkoxycarbonyl, or haloalkoxycarbonyl for example, no salt formation occurs.

The compounds of this invention, wherein $R_3$ of the above formula is hydrogen, can be prepared by selectively reducing the centers of unsaturation of the naturally occurring nitrogeneous, polycarbocyclic trienes of the formula

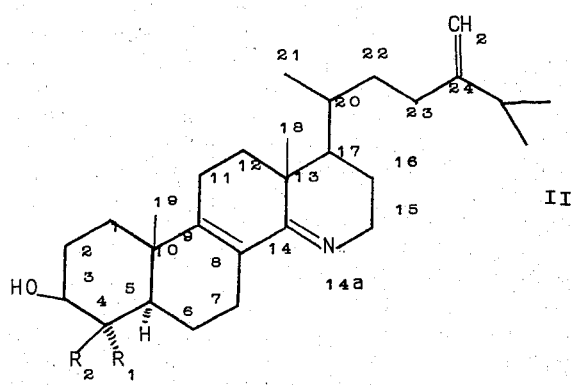

II in which $R_1$ and $R_2$ are both hydrogen or both methyl.

The compounds described hereinbelow are named according to the accepted steroid nomenclature system by following the numbering system shown in the above formula. The dashed bonding lines between atoms, such as the carbon-hydrogen bond at $C_5$ for example, indicate the $\alpha$-configuration. The solid bonding lines, such as the carbon-oxygen bond at $C_3$ for example, indicate the $\beta$-configuration. The starting materials for the compounds of this invention are all characterized as having the cholestanol configuration in that the hydroxyl group at $C_3$, for example, is of the $\beta$-configuration, while the hydrogen at $C_5$ is of the $\alpha$-configuration. The compounds are named as cholestane derivatives. For example, a typical starting material is named as 3$\beta$-hydroxy-24-methylene-5$\alpha$-14a-aza-D-homo-cholesta-8(9),14(14a)-diene. The compounds provided by this invention will have the stereochemistry of the starting material except at the sites where reduction has been effected. In particular, reduction of the $C_8$-$C_9$ double bond, as described hereinbelow, normally provides compounds with a $\beta$ hydrogen at $C_8$ and an $\alpha$ hydrogen at $C_9$. Reduction of the $C_{14}$-$N_{14a}$ imine bond generally provides a mixture of stereoisomers that consists predominantly of an $\alpha$ configuration at $C_{14}$. Therefore, when reference is made herein to the reduced $C_{14}$ position, it will be understood that both the $\alpha$ and $\beta$ isomers are included. Similarly, the reduction of the $C_{24}$-methylene group affords a mixture of isomers. Both of the isomers, as well as the mixture thereof, are a part of this invention. The nomenclature for the compounds provided by this invention has been simplified throughout this application by omitting the $\alpha$ and the $\beta$ stereochemical designations. For example, the starting material named above will hereinafter be referred to as 3-hydroxy-24-methylene-14a-aza-D-homo-cholesta-8(9),14(14a)-diene.

By proper selection of reducing agents and reaction conditions, the ring unsaturation of the starting trienes of the above formula can be reduced preferentially over the side chain unsaturation. Furthermore, either ring double bond can be reduced without affecting to a great extent the other sites of unsaturation. Because the side chain reduction is generally accomplished by catalytic hydrogenation, the side chain double bond normally cannot be selectively reduced without affecting the ring unsaturation.

The 3-hydroxy-24-methylene-14a-aza-D-homo-cholest-8(9)-enes of this invention are prepared by selectively reducing the $C_{14}$-$N_{14a}$ double bond of a triene having the above formula. Selective reduction of the $C_{14}$-$N_{14a}$ double bond can be accomplished by using a hydride reducing agent such as an alkali metal hydride or borohydride, or an alkoxy metal hydride. Examples of such reducing agents include lithium aluminum hydride, sodium borohydride, potassium borohydride, lithium trimethoxy aluminum hydride, sodium trimethoxy borohydride, lithium tri-tert-butoxy aluminum hydride, and the like. Reducing agents such as diborane or disiamylborane can also be employed if desired. The preferred reducing agents are the alkali metal borohydrides. The reduction is best carried out in any of a number of unreactive organic solvents, including ethers, such as diethyl ether, diisopropyl ether, tetrahydrofuran, dioxane or diglyme; or alcohols, such as methanol, ethanol, isopropyl alcohol or t-butyl alcohol.

Reaction times vary widely depending upon the choice of the reducing agent, solvent medium, and the temperature at which the reaction is carried out. Normally, the reaction is carried out at a temperature between about 20° and about 80°C. When the reaction is carried out using sodium borohydride in isopropyl alcohol as a reducing agent, at a temperature of about 20° to 30°C., for instance, the reduction of the $C_{14}$-$N_{14a}$ double bond of the triene starting material is essentially complete within about 1 to 8 hours. After the reduction is complete, the solvent is evaporated and the excess reducing agent is decomposed by the addition of a proton source, such as water for example. The product can be isolated by extraction into a water-immiscible solvent such as ethyl acetate, diethyl ether or dichloromethane. Evaporation of the solvent from the organic extracts affords the product as a free base, which may be further purified if desired by chromatography or crystallization, for example. Alternatively, the product can be isolated as an addition salt by the addition of an appropriate acid, for instance acetic acid. When an acid addition salt is to be employed for isolation, the free base is dissolved in an appropriate inert solvent, such as ethyl acetate or diethyl ether, and an appropriate acid can be added, whereupon the acid addition salt of 3-hydroxy-24-methylene-14a-aza-D-homo-cholest-8(9)-ene normally precipitates and can be collected by filtration.

3-Hydroxy-24-methylene-14a-aza-D-homo-cholest-14(14a)-enes are prepared by reducing the $C_8$-$C_9$ double bond of the triene starting material. Because the $C_8$-$C_9$ double bond is less reactive toward reduction than the $C_{14}$-$N_{14a}$ double bond, stronger reducing conditions are generally employed. As a consequence, it is more difficult to selectively reduce the $C_8$-$C_9$ double bond. Dissolving metal reduction conditions can be employed to obtain the diene; however, some concurrent reduction of the $C_{14}$-$N_{14a}$ double bond is sometimes observed. The 24-methylene-$\Delta^{14(14a)}$ olefins are readily separated from the 24-methylene-$\Delta^{8(9)}$ olefins by employing commonly used separation techniques such as solid-liquid chromatography, thick layer chromatography, gas-liquid chromatography, crystallization, or the like.

The reduction of the $C_8$-$C_9$ double bond of the triene starting material is best carried out with a solution of an alkali or alkaline earth metal in liquid ammonia. The preferred metals include lithium, sodium and potassium; however, metals such as calcium and magnesium can also be used. The reaction may be carried out in the presence of a suitable co-solvent for the triene if desired. Suitable co-solvents include those of the ether class, especially diethyl ether, tetrahydrofuran, 1,2-dimethoxyethane, or dioxane. If co-solvents are omitted, however, good results are also obtained. The temperature of the reaction can be in the range of about −70°C. to the boiling point of liquid ammonia, generally about −33°C. Preferably, the temperature is maintained in the range of about −65° to about −33°C. After the reaction is complete, any excess reducing agent is decomposed by adding a proton source, such as an alcohol, for example methanol or ethanol, or water, or an aqueous ammonium chloride solution. The ammonia, and the co-solvent if one was used, is evaporated from the reaction mixture and the product is isolated therefrom by extraction with a water immiscible solvent, such as diethyl ether, ethyl acetate, or the like. Concentration of the solvent provides the product, which can be further purified if desired by normal techniques such as chromatography, recrystallization, or the like.

Further reduction of a 3-hydroxy-24-methylene-14a-aza-D-homo-cholest-14(14a)-ene under controlled conditions effects reduction of the $C_{14}$–$N_{14a}$ double bond to provide tetrahydro derivatives of the starting triene. In particular, the $C_{14}$–$N_{14a}$ double bond of the above-described diene can be reduced by essentially the same reaction conditions as required to reduce the $C_{14}$–$N_{14a}$ double bond of the naturally occurring triene. The diene is reduced with a metal hydride such as sodium borohydride, generally in a solvent such as isopropyl alcohol. The reaction is normally carried out at a temperature of about 20° to 30°C., and generally is complete after about 2 to 20 hours.

It should be noted that once the $C_{14}$–$N_{14a}$ double bond of the starting triene has been reduced, the $C_8$–$C_9$ double bond becomes substantially resistant to reduction under normal conditions.

Saturated aza-sterols provided by the present invention are hexahydro derivatives of the starting trienes and are generally prepared by further reduction of the 24-methylene tetrahydro compounds wherein both the $C_8$–$C_9$ and the $C_{14}$–$N_{14a}$ double bonds are reduced. More specifically, the saturated compounds of the invention are preferably prepared by catalytic hydrogenation of a 24-methylene-14a-aza-D-homo-cholestane. Alternatively, catalytic reduction under forcing conditions of the starting triene provides the fully saturated aza-sterols. Mild catalytic reduction of the triene, however, effects reduction only of the $C_{14}$–$N_{14a}$ double bond and of the 24-methylene group.

The catalytic hydrogenation of a 24-methylene-14a-aza-D-homo-cholestane can be accomplished by reaction with hydrogen gas under a suitable pressure and in the presence of a suitable hydrogenation catalyst, normally in an unreactive organic solvent. The reaction is generally carried out in a hydrogen atmosphere at a pressure of about 1 to about 5 atmospheres. Suitable hydrogenation catalysts include a variety of metal catalysts such as nickel, ruthenium, palladium, osmium, platinum, and certain metal oxides, especially platinum oxide. Reaction temperatures are usually maintained in the range of about 15° to about 50°C., although higher temperatures may be used, if desired. The reaction times vary, depending upon the choice of catalyst, temperature, and hydrogen pressure, but normally the reaction is essentially complete within 2 to 48 hours. Suitable unreactive solvents include ethers, esters, alcohols, and water. Examples of preferred solvents are diethyl ether, dioxane, tetrahydrofuran, ethyl acetate, methanol and ethanol. When the reaction is complete, the catalyst is filtered off and the filtrate is evaporated to give the 24-methyl-14a-aza-D-homo-cholestane derivative as the free base. Purification can be accomplished by any of the common methods such as, for example, chromatography or crystallization. Alternatively, the free base can be converted to a salt, especially an acid addition salt, for example by proper adjustment of the pH. The acid addition salts can be purified if desired by recrystallization, and the salts can be converted back to the free bases by simple hydrolysis with a suitable base. For example, treatment of an acid addition salt with a molar equivalent of a base such as sodium hydroxide, potassium hydroxide or triethylamine, affords the free base of a compound of the present invention.

Turning now to the preparation of derivatives of the reduction products of the starting trienes, the 3-hydroxy-24-methylene-14a-aza-D-homo-cholest-14(14a)-enes are converted to compounds in which the hydroxyl group is derivatized by procedures familiar to those skilled in organic chemistry. For example, a 3-hydroxy-24-methylene-$\Delta^{14(14a)}$ olefin can be converted to a 3-alkanoyloxy-24-methylene-$\Delta^{14(14a)}$ olefin by reaction with a reactive acid derivative such as, for example, an acid halide, especially an acid chloride or an acid bromide; an acid anhydride, or a mixed acid anhydride. Preferably, a 3-hydroxy-24-methylene-$\Delta^{14(14a)}$ olefin is reacted with a $C_1$ to $C_4$ alkanoic acid anhydride or mixed anhydride, such as acetic anhydride or formic-acetic anhydride for example, in the presence of a suitable base such as pyridine, triethylamine, N-methylmorpholine, or the like. The reactants are normally added in equimolar quantities, although an excess of either can be used if desired. Solvents may be employed when the base being used does not itself act as a solvent. Suitable solvents are unreactive organic solvents such as esters, ketones, haloalkanes and aromatic solvents. Preferred solvents include ethyl acetate, acetone, dichloromethane and benzene. The 3-alkanoyloxy-24-methylene-14a-aza-D-homo-cholest-14(14a)-enes are readily hydrolyzed back to the 3-hydroxy compound in the presence of a base, such as sodium or potassium hydroxide, or an acid, such as hydrochloric or sulfuric acid for example.

3-Alkoxycarbonyloxy and 3-haloalkoxycarbonyloxy-24-methylene-14a-aza-D-homo-cholest-14(14a)-enes are readily prepared by reaction of a 3-hydroxy-24-methylene-$\Delta^{14(14a)}$ olefin with a suitable acylating agent, preferably of the chloroformate class, especially a $C_1$ to $C_4$-alkylhaloformate or a halo $C_1$–$C_4$-alkylhaloformate. Specifically, treatment of a 3-hydroxy-24-methylene-$\Delta^{14(14a)}$ olefin with an alkyl chloroformate, for example ethyl chloroformate, in a suitable solvent such as dichloromethane, acetone, ethyl acetate, or the like, in the presence of a base, such as triethylamine or pyridine, followed by removal of the solvent, affords a 3-alkoxycarbonyloxy-24-methylene-$\Delta^{14(14a)}$ olefin of the invention. These compounds are readily hydrolyzed back to the 3-hydroxy compounds by treatment with a base or an acid. The haloalkoxycarbonyloxy derivatives are prepared in the same manner, starting with a suitable haloalkylhaloformate such as, for example, 2,2,2-trichloroethyl chloroformate. These compounds are also readily hydrolyzed in the presence of acid or base to the 3-hydroxy precursor.

For the preparation of derivatives of 3-hydroxy-24-methylene-$\Delta^{8,9}$ olefins, 3-hydroxy-24-methylene tetrahydro, and 3-hydroxy-24-methyl tetrahydro compounds, care must be exercised because of the presence of two reactive sites in these molecules. In particular, all of these compounds have a reduced 14a-aza group in addition to a 3-hydroxy group. For example, treatment of any of these 3-hydroxy-14a-aza compounds with an acylating agent such as an acid halide or an anhydride, affords a 3-acyloxy-N-acyl compound.

The 3-acyloxy group is readily hydrolyzed under relatively mild conditions with acid or base to the 3-hydroxy group, whereas the N-acyl group is stable to hydrolysis under such mild conditions. For example, a 3-alkanoyloxy-24-methylene-14a-aza-D-homo-14a-alkanoyl-cholestane can be treated with an aqueous base, such as sodium or potassium hydroxyide, in a solvent such as methanol or ethanol and at a temperaure of about 20° to 80°C. for 1 to 2 hours, thereby cleaving the 3-alkanoyl group to the corresponding 3-hydroxy group without affecting the N-alkanoyl group at the 14a- position.

In a further aspect of the invention, the starting triene can first be derivatized at the 3-hydroxyl group and subsequently reduced to provide compounds unsubstituted at the reduced 14a-aza position. For example, catalytic hydrogenation of a 3-alkanoyloxy-24-methylene-14a-aza-D-homo-cholesta-8(9),14(14a)-diene can provide the 3-alkanoyloxy-24-methyl-14a-aza-D-homo-cholest-8(9)-ene. Mild reduction, as described hereinbefore with an agent such as sodium borohydride in isopropyl alcohol for example, of such a derivatized triene effects reduction of the $C_{14}$–$N_{14a}$ double bond. Subsequent hydrogenation then effects reduction of the 24-methylene group.

The 3-alkanoyloxy compounds of this invention can also be prepared by transesterification of the 3-hydroxy precursor. For example, a 3-hydroxy-24-methylene-14a-aza-D-homo-cholestane can be treated with an ester, for example ethyl formate or methyl acetate, thereby providing the corresponding 3-alkanoyloxy derivative. The transesterification reaction is generally carried out at a temperature of about 20° to 80°C., and is normally complete after about 2 to 10 days.

Compounds which are unsaturated at the $C_{14}$–$N_{14a}$ position can be converted to quaternary immonium salts by reaction with an alkylating agent such as methyl iodide or ethyl sulfate. Additionally, compounds which have been reduced at the $C_{14}$–$N_{14a}$ position can be converted to the corresponding N-alkylated derivative by reaction with an alkylating agent. Typically, the alkylation reaction is carried out in a solvent, normally at a temperature of about 20° to 120°C. Further alkylation provides quaternary ammonium salts.

Typical examples of specific compounds of the present invention are listed below:
3-hydroxy-24-methylene-14a-aza-D-homo-cholest-14(14a)-ene;
3-hydroxy-24-methylene-14a-aza-D-homo-4,4-dimethyl-cholest-14(14a)-ene;
3-hydroxy-24-methylene-14a-aza-D-homo-cholest-8(9)-ene;
3-hydroxy-24-methylene-14a-aza-D-homo-4,4-dimethyl-cholest-8(9)-ene;
3-hydroxy-24-methylene-14a-aza-D-homo-cholestane;
3-hydroxy-24-methylene-14a-aza-D-homo-4,4-dimethyl-cholestane;
3-hydroxy-24-methyl-14a-aza-D-homo-cholestane;
3-hydroxy-4,4,24-trimethyl-14a-aza-D-homo-cholestane;
3-acetoxy-24-methylene-14a-aza-D-homo-cholest-14(14a)-ene;
3-acetoxy-24-methylene-14a-aza-D-homo-14a-acetyl-cholest-8(9)-ene;
3-hydroxy-24-methylene-14a-aza-D-homo-14a-acetyl-cholest-8(9)-ene;
3-hydroxy-24-methyl-14a-aza-D-homo-14a-acetyl-cholestane;
3-O-formyl-24-methylene-14a-aza-D-homo-14a-formyl-cholestane;
3-O-formyl-24-methyl-14a-aza-D-homo-14a-acetyl-cholestane;
3-O-formyl-24-methylene-14a-aza-D-homo-cholestane;
3-hydroxy-14a,24-dimethyl-14a-aza-D-homo-cholestane;
3-O-formyl-24-methylene-14a-aza-D-homo-cholest-14(14a)-ene;
3-hydroxy-24-methylene-14a-aza-D-hono-14a-acetyl-cholestane;
3-acetoxy-24-methyl-14a-aza-D-homo-14a-ethyl-cholestane;
3-acetoxy-24-methyl-14a-aza-D-homo-14a-propyl-cholestane;
3-O-formyl-24-methyl-14a-aza-D-homo-cholestane;
3-hydroxy-24-methylene-14a-aza-D-homo-cholest-8(9)-enium acetate;
3-O-formyl-24-methylene-14a-aza-D-homo-cholest-8(9)-enium chloride;
3-propionyloxy-24-methyl-14a-aza-D-homo-cholestane;
3-ethoxycarbonyloxy-24-methylene-14a-aza-D-homo-14a-ethoxycarbonyl-cholestane;
3-(2,2,2-trichloroethoxycarbonyl)oxy-24-methylene-14a-aza-D-homo-14a-(2,2,2-trichloroethoxycarbonyl)-cholestane;
3-hydroxy-24-methyl-14a-aza-D-homo-14a-(2,2,2-trichloroethoxycarbonyl)-cholestane; and
3-acetoxy-24-methylene-14a-azonia-D-homo-14a-methyl-cholestane iodide.

As hereinbefore indicated, the starting materials required for preparing the compounds of this invention are 24-methylene-14a-aza-D-homo-cholesta-8(9),14(14a)-diene derivatives. These triene substances are prepared by culturing the strain of *Geotrichum flavo-brunneum*, NRRL 3862, which strain is in the permanent culture collection of the Agricultural Research Service, Northern Utilization Research and Development Division, Department of Agriculture, Peoria, Ill. The organic which is cultured was isolated by the standard serial dilution procedure from a soil sample collected in the Grand Teton National Park region of Wyoming. The organism is described in detail by Miller, et al., *Mycologia*, 49, 779–808, 1957. The preparation and isolation of the starting material used in the present invention is the subject of co-pending U.S. patent application Ser. No. 327,171, filed Feb. 2, 1973, and is carried out as described hereinbelow.

A culture of *Geotrichum flavo-brunneum* is grown under submerged aerobic conditions in a fermentation medium comprising carbohydrates, amino acids, and nutrient inorganic salts. The organism is grown for about 3 days at a temperature of about 20° to 35°C. After the fermentation is complete, the fermentation mycelium is extracted with a suitable organic solvent, such as ethyl acetate or amyl acetate for instance. Evaporation of the solvent from the combined organic extracts provides a mixture of compounds. The starting materials for the present invention are separated from the mixture by chromatography and crystallization.

The compounds provided by the present invention are useful for combating infections of fungal origin. In particular, the compounds inhibit fungal growth when applied to environmental surfaces such as shower stalls, foot baths, exterior surfaces of wood, concrete, brick, or the like, as well as to skin surfaces affected by fungal growth. The compounds are most conveniently formulated for use as a solution or suspension with a suitable diluent, excipient, or carrier. Typical diluents and carriers include water, alcohol, glycols, and the like. Additionally, the compound can be formulated as a cream or ointment with suitable carriers such as hydrocarbon waxes, polyethylene glycol, or a cold cream base for example.

The following detailed examples are presented for the purpose of illustration only and are not to be construed as limiting the invention in scope. In general, the compounds described hereinbelow were characterized by mass spectral analysis, melting point, infrared absorptions given in wave numbers ($cm^{-1}$), and proton magnetic resonances given in delta values δ, (parts per million).

PREPARATION 1

The production of the starting materials required for the present invention is illustrated by the following procedure.

Spores of *Geotrichum flavo-brunneum* strain NRRL 3862 were inoculated on a nutrient agar slant having the following composition:

| Agar Slant Medium | |
|---|---|
| Ingredient | Weight/Volume (g./l.) |
| Glucose | 20 |
| Peptone | 5 |
| Potassium Dihydrogen Phosphate | 0.5 |
| Magnesium Sulfate | 0.02 |
| Ferrous Sulfate | 0.01 |
| Agar | 20 |

The above cultures were incubated at a temperature of 25°C. for 7 days. A loop of spores from the slant culture was transferred to a vegetative inoculum having the following composition:

| Vegetative Medium | |
|---|---|
| Ingredient | Weight/Volume (g./l.) |
| Sucrose | 25 |
| Edible Molasses | 36 |
| Corn Steep | 6 |
| Potassium Dihydrogen Phosphate | 2 |
| NZ Case[1] | 10 |
| Tap Water | |

[1]Enzymatic digest of casein, Scheffield Chemical Co., Norwich, N.Y.

The inoculated vegetative medium was shaken on a rotary shaker at 250 r.p.m. for about 24 to 48 hours at a temperature of about 25°C. Five percent of the volume of the vegetative inoculum containing viable vegetative growth was employed to inoculate a fermentation medium having the following composition:

| Fermentation Medium | |
|---|---|
| Ingredient | Weight/Volume (g./l.) |
| Glucose | 25 |
| Corn Starch | 10 |
| Peptone (meat) | 10 |
| NZ Amine A[1] | 4 |
| Molasses | 5 |
| Magnesium Sulfate Heptahydrate | 5 |
| Calcium Carbonate | 2 |

| -continued Fermentation Medium | |
|---|---|
| Ingredient | Weight/Volume (g./l.) |
| Tap Water | |

[1]Pancreatic hydrolysate of casein, Scheffield Chemical Company, Norwich, N.Y.

The inoculated fermentation medium was agitated continuously for 72 hours at a temperature of 25°C. Throughout the fermentation, sterile air was passed through the fermentation medium at a rate of one half volume of air per volume of fermentation medium per minute.

Upon completion of the fermentation, the fermentation broth was extracted several times with ethyl acetate. The combined ethyl acetate extracts were concentrated to an oil residue. The residue was dissolved in a 20 percent acetone solution in n-hexane. Additional hexane was added to the mixture, and the solution was cooled to −20°C. whereupon 3-hydroxy-24-methylene-14a-aza-D-homo-cholesta-8(9),14(14a)-diene crystallized. The crystals were collected by filtration and air dried, m.p. 115°–118°C. The filtrate was concentrated to dryness, providing an oily residue which was dissolved in a mixture of ethyl acetate-hexane-distilled water (80:16:4). The solution was passed over a column packed with basic alumina (Woelm grade W200, Water Associates, Inc., Framingham, Mass.). The column was eluted with the same solvent mixture, and eluate fractions of 1 liter volume each were collected. Eluate fractions 9 through 23 were combined and the solvent was removed therefrom under reduced pressure to provide a residue which was crystallized from acetone. The crystals were collected by filtration and identified as 3-hydroxy-24-methylene-14a-aza-D-homo-4,4-dimethyl-cholesta-8(9),14(14a)-diene, m.p. 147°C.

EXAMPLE 1

3-Hydroxy-24-methylene-14a-aza-D-homo-cholest-14(14a)-ene

To a solution of 1 g. of 3-hydroxy-24-methylene-14a-aza-D-homo-cholesta-8(9),14(14a)-diene in 80 cc. of liquid ammonia and 20 cc. of tetrahydrofuran (THF) were added five 200 mg. portions of lithium metal over a 1 hour period. After the addition was complete, the reaction mixture was stirred for 1 hour at ambient temperature. A 10 percent aqueous ammonium chloride solution was added to the reaction mixture until the dark color of the mixture was dissipated. The ammonia and THF solvents were evaporated under reduced pressure and the remaining aqueous suspension was extracted with ethyl acetate. The organic extracts were combined and washed with saturated aqueous sodium bicarbonate solution and dried over magnesium sulfate. Filtration of the drying agent and evaporation of the filtrate under reduced pressure afforded 885 mg. of a yellow oil which was shown by thin layer chromatography to consist of essentially two components. The mixture was separated by column chromatography over a 1 × 8 inch neutral alumina support and eluted with ethyl acetate. Fractions 4 to 11, each containing 40 cc., were combined and evaporated to dryness under reduced pressure to give 353 mg. of 3-hydroxy-24-methylene-14a-aza-D-homo-cholest-14(14a)-ene as a pale yellow oil. m/e: $M^+$ 413; IR ($CHCl_3$): 1640 $cm^{-1}$: C=N; nmr ($CDCl_3$): δ4.70 (d, 2H), 24-methylene.

EXAMPLE 2

3-Hydroxy-24-methylene-14a-aza-D-homo-cholest-8(9)-ene

A solution of 5 g. of 3-hydroxy-24-methylene-14a-aza-D-homo-cholesta-8(9),14(14a)-diene in 30 cc. of isopropyl alcohol was stirred at room temperature for 2 hours with 500 mg. of sodium borohydride. The solvent was evaporated under reduced pressure and the residue was dissolved in ethyl acetate. The ethyl acetate solution was washed with water and dried, and the solvent was evaporated under reduced pressure. Five grams of 3-hydroxy-24-methylene-14a-aza-D-homo-cholest-8(9)-ene was obtained as an oil; m/e: M$^+$ 412.

EXAMPLE 3

3-Hydroxy-24-methylene-14a-aza-D-homo-cholest-8(9)-enium acetate

A solution of 5 g. of 3-hydroxy-24-methylene-14a-aza-D-homo-cholest-8(9)-ene in 15 cc. of ethyl acetate was cooled to 5°C. and stirred. To the cold solution was added 720 mg. of glacial acetic acid. After adding 50 cc. of diethyl ether to the reaction mixture, white crystals precipitated and were collected by filtration and air dried to afford 4.26 g. of the acetic acid salt of 3-hydroxy-24-methylene-14a-aza-D-homo-cholest-8(9)-ene. M.P. 173°–175°C.; IR (CHCl$_3$): 3400 cm$^{-1}$ N$^+$H$_2$; nmr (CDCl$_3$): δ4.69 (d, 2H) 24-methylene; δ3.27 (s, 1H) C-14 hydrogen; δ7.3 (s, 2H) N$^+$H$_2$.

EXAMPLE 4

3-Hydroxy-24-methylene-14a-aza-D-homo-cholestane

Two-hundred milligrams of sodium borohydride was added to a solution of 450 mg. of 3-hydroxy-24-methylene-14a-aza-D-homo-cholest-14(14a)-ene in 30 cc. of isopropyl alcohol at room temperature. The reaction mixture was stirred for 12 hours at room temperature, after which the solvent was evaporated under reduced pressure and the residue was dissolved in 30 cc. of water. The product was insoluble in the aqueous mixture and was extracted therefrom into ethyl acetate. The organic extracts were combined, washed with water, and dried over potassium carbonate. Filtration of the drying agent and evaporation of the filtrate under reduced pressure afforded 430 mg. of 3-hydroxy-24-methylene-14a-aza-D-homo-cholestane as an oil. m/e: M$^+$ 415; IR (CHCl$_3$): 3430 cm$^{-1}$ NH; nmr (CDCl$_3$): δ4.68 (d, 2H) 24-methylene.

EXAMPLE 5

3-Hydroxy-24-methyl-14a-aza-D-homo-cholestane

Fifty milligrams of platinum oxide was added to a solution of 220 mg. of 3-hydroxy-24-methylene-14a-aza-D-homo-cholestane in 25 cc. of ethyl acetate. The mixture was agitated for 16 hours at room temperature under hydrogen gas at one atmosphere pressure. The catalyst was filtered off and washed with 20 cc. of chloroform. The organic filtrate was evaporated to dryness under reduced pressure, affording 200 mg. of the desired compound as an oil. The oil was crystallized from ethyl acetate and pentane to give 200 mg. of 3-hydroxy-24-methyl-14a-aza-D-homo-cholestane. m/e: M$^+$ 417.

EXAMPLE 6

3-Acetoxy-24-methylene-14a-aza-D-homo-14a-acetyl-cholest-8(9)-ene

A solution of 1 g. of 3-hydroxy-24-methylene-14a-aza-D-homo-cholest-8(9)-ene in 20 cc. of pyridine was cooled to 0°C. in an ice bath. To the cold solution was added 3.0 cc. of acetic anhydride and the reaction mixture was allowed to warm to room temperature and was stirred for 12 hours. Evaporation of the solvent under reduced pressure afforded 1.05 g. of an oil which was crystallized from hexane to give 3-acetoxy-24-methylene-14a-aza-D-homo-14a-acetyl-cholest-8(9)-ene. M.P. 122°–123°C.; m/e: M$^+$ 497; IR(CHCl$_3$): 1730 cm$^{-1}$

1645 cm$^{-1}$

nmr (CDCl$_3$): δ2.0 (s, 6H)

δ4.72 (d, 2H) 24-methylene.

EXAMPLE 7

3-Hydroxy-24-methylene-14a-aza-D-homo-14a-acetyl-cholest-8(9)-ene

A solution of 200 mg. of 3-acetoxy-24-methylene-14a-aza-D-homo-14a-acetyl-cholest-8(9)-ene in 20 cc. of methyl alcohol was heated at reflux for two hours with 1 cc. of 5N sodium hydroxide. After cooling the reaction mixture to room temperature and evaporating the solvent under reduced pressure, 50 cc. of water was added to the residue. The product was insoluble in water and was extracted therefrom into diethyl ether. The ethereal extracts were combined and washed with water and dried over magnesium sulfate. Filtration of the drying agent and evaporation of the filtrate under reduced pressure gave 150 mg. of 3-hydroxy-24-methylene-14a-aza-D-homo-14a-acetyl-cholest-8(9)-ene. m/e: M$^+$ 455; IR(CHCl$_3$): 1640 cm$^{-1}$

nmr (CDCl$_3$) δ1.98 (s, 3H)

δ4.68 (d, 2H) 24-methylene.

EXAMPLE 8

3-O-formyl-24-methylene-14a-aza-D-homo-cholest-8(9)-ene

A solution of 150 mg. of 3-hydroxy-24-methylene-14a-aza-D-homo-cholest-8(9)-ene in 25 cc. of ethyl formate was heated at reflux for three days. The reaction mixture was cooled and evaporated to dryness under reduced pressure, affording 3-O-formyl-24-methylene-14a-aza-D-homo-cholest-8(9)-ene as an oil.

EXAMPLE 9

3-O-formyl-24-methylene-14a-aza-D-homo-14a-formyl-cholest-8(9)-ene

A solution of 5 cc. of formic-acetic anhydride was cooled to 5°C. in an ice bath and 200 mg. of the acetate salt of 3-hydroxy-24-methylene-14a-aza-D-homo-cholest-8(9)-ene was added. The reaction mixture was stirred for 16 hours while warming to room temperature. The solvent was evaporated to dryness under reduced pressure and the residual oil was dissolved in 50 cc. of ethyl acetate. The solution was washed with saturated aqueous sodium bicarbonate solution and with water, and dried over magnesium sulfate. Filtration of the drying agent and evaporation of the filtrate under reduced pressure afforded 190 mg. of an oil which crystallized from hexane. Recrystallization from methanol-water afforded 130 mg. of 3-O-formyl-24-methylene-14a-aza-D-homo-14a-formyl-cholest-8(9)-ene. M.P. 121°–123°C.; m/e: M$^+$ 469; IR(CHCl$_3$): 1730 cm$^{-1}$

1665 cm$^{-1}$

nmr (CDCl$_3$): δ4.7 (d, 2H); 24-methylene; δ7.68 (s, 1H)

δ8.08 (s, 1H)

I claim:

1. The compound of the formula

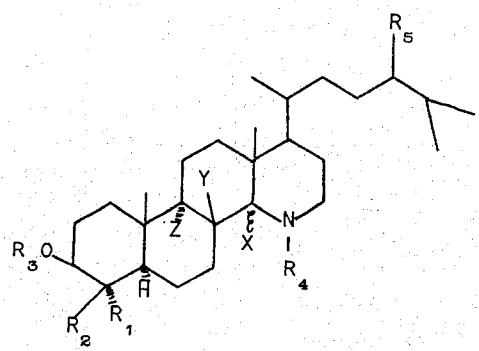

wherein:

$R_1$ and $R_2$ are both hydrogen or both methyl;

$R_3$ is hydrogen, $C_1$–$C_4$ alkanoyl, $C_1$–$C_4$ alkoxycarbonyl, or halo $C_1$–$C_4$ alkoxycarbonyl;

$R_4$ is hydrogen, $C_1$–$C_4$ alkyl, $C_1$–$C_4$ alkanoyl, $C_1$–$C_4$ alkoxycarbonyl, or halo $C_1$–$C_4$ alkoxycarbonyl, and X is hydrogen, or $R_4$ and X when taken together form a double bond;

Y and Z are both hydrogen or taken together form a double bond;

$R_5$ is methyl or methylene, but is methyl only when X, Y, and Z are all hydrogen;

with the limitation that either X or both Y and Z must be hydrogen; and the pharmaceutically acceptable salts thereof.

2. The compound of claim 1 wherein Y and Z are both hydrogen and X together with $R_4$ forms a double bond.

3. The compound of claim 2 wherein $R_1$ and $R_2$ are both hydrogen.

4. The compound of claim 3 wherein $R_3$ is hydrogen.

5. The compound of claim 3 wherein $R_3$ is acetyl.

6. The compound of claim 1 wherein X is hydrogen and Y and Z together form a double bond.

7. The compound of claim 6 wherein $R_1$ and $R_2$ are both hydrogen.

8. The compound of claim 7 wherein $R_3$ is hydrogen.

9. The compound of claim 8 wherein $R_4$ is hydrogen.

10. The compound of claim 8 wherein $R_4$ is acetyl.

11. The compound of claim 8 wherein $R_4$ is formyl.

12. The compound of claim 7 wherein $R_3$ and $R_4$ are both ethoxycarbonyl.

13. The compound of claim 7 wherein $R_3$ and $R_4$ are both 2,2,2-trichloroethoxycarbonyl.

14. The compound of claim 1 wherein X, Y and Z are all hydrogen.

15. The compound of claim 14 wherein $R_1$, $R_2$, $R_3$ and $R_4$ are all hydrogen.

16. The compound of claim 15 wherein $R_5$ is methylene.

17. The compound of claim 15 wherein $R_5$ is methyl.

* * * * *